United States Patent
Glabe et al.

(10) Patent No.: US 6,770,448 B2
(45) Date of Patent: Aug. 3, 2004

(54) FLUORESCENT AMYLOID Aβ PEPTIDES AND USES THEREOF

(75) Inventors: Charles Glabe, Irvine, CA (US); William Garzon Rodriguez, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/455,218

(22) Filed: Jun. 5, 2003

(65) Prior Publication Data

US 2003/0204051 A1 Oct. 30, 2003

Related U.S. Application Data

(62) Division of application No. 09/133,866, filed on Aug. 13, 1998, now Pat. No. 6,600,017.
(60) Provisional application No. 60/055,660, filed on Aug. 14, 1997.

(51) Int. Cl.[7] ................................................ G01N 33/53
(52) U.S. Cl. ........................... 435/7.1; 436/15; 436/800
(58) Field of Search ............................. 435/7.1; 436/15, 436/800

(56) References Cited

U.S. PATENT DOCUMENTS

| | | |
|---|---|---|
| 5,166,322 A | 11/1992 | Shaw et al. |
| 5,434,050 A | 7/1995 | Maggio et al. |
| 5,506,097 A | 4/1996 | Potter et al. |
| 5,721,106 A | 2/1998 | Maggio et al. |
| 5,777,078 A | 7/1998 | Bayley et al. |
| 5,780,265 A | 7/1998 | Dennis et al. |
| 5,786,328 A | 7/1998 | Dennis et al. |
| 5,854,204 A | 12/1998 | Findeis et al. |

FOREIGN PATENT DOCUMENTS

| | | |
|---|---|---|
| WO | WO93/04194 | 3/1993 |
| WO | WO 94/28412 | 12/1994 |
| WO | WO97/07402 | 2/1997 |

OTHER PUBLICATIONS

Abraham et al., "Immunochemical Identification of the Serine Protease Inhibitor $\alpha_1$–Antichymotrypsin in the Brain Amyloid Deposits of Alzheimer's Disease" *Cell* 52:487–501 (1988).

Barrow et al., "Solution Conformations and Aggregational Properties of Synthetic Amyloid β–Peptides of Alzheimer's Disease" *J. Mol. Biol.* 225:1075–1093 (1992).

Barrow et al., "Solution Structures of β Peptide and Its Constituent Fragments: Relation to Amyloid Deposition" *Science* 253:179–182 (1991).

Burdick et al., "Assembly and Aggregation Properties of Synthetic Alzheimer's A4/β Amyloid Analogs" *J. Biol. Chem.* 267:546–554 (1992).

Bush et al., "Modulation of Aβ Adhesiveness and Secretase Site Cleavage by Zinc" *J. Biol. Chem.* 269:12152–12158 (1994).

Bush et al., "Rapid induction of Alzheimer A beta amyloid formation by zinc" *Science* 265:1464–1467 (1994).

Fraser et al., "pH–Dependent Structural Transitions of Alzheimers Amyloid Peptides" *Biophys. J.* 60:1190–1201 (1991).

(List continued on next page.)

*Primary Examiner*—Gary Kunz
*Assistant Examiner*—Sharon Turner
(74) *Attorney, Agent, or Firm*—Clark & Elbing LLP

(57) ABSTRACT

Disclosed herein are aggregating amyloid Aβ peptides which are covalently bonded (for example, at a cysteine amino acid residue) to a fluorescent label, and methods for their use.

14 Claims, 10 Drawing Sheets

OTHER PUBLICATIONS

Halverson et al., "Molecular Determinants of Amyloid Deposition in Alzheimer's Disease; Conformational Studies of Synthetic β–Protein Fragments" *Biochemistry* 29:2639–2644 (1990).

Hilbich et al., "Aggregation and Secondary Structure of Synthetic Amyloid βA4 Peptides of Alzheimer's Disease" *J. Mol. Biol.* 218:149–163 (1991).

Inouye et al., "Structure of β–Crystallite Assemblies Formed by Alzheimer β–amyloid Protein Analogues: Analysis by X–Ray Diffraction" *Biophys. J.* 64:502–19 (1994).

Jarrett et al., "The Carboxy Terminus of the β Amyloid Protein Is Critical For The Seeding of Amyloid Formation: Implications for the Pathogenesis of Alzheimer's Disease" *Biochemistry* 32:4693–4697 (1993).

Kirschner et al., "Synthetic Peptide Homologous to β Protein From Alzheimer Disease Forms Amyloid–like fibrils in Vitro" *Proc. Natl. Acad. Sci. USA* 84:6953–6957 (1986).

Maggio et al., "Reversible In Vitro Growth Of Alzheimer Disease β–amyloid Plaques By Deposition of Labeled Amyloid Peptide" *Proc. Natl. Acad. Sci. USA* 89:5462–5466 (1992).

Miyakawa et al., "Ultrastructural Study of Senile Plaques and Microvessels in the Brain With Alzheimer's Disease and Down's Syndrome" *Ann. Med.* 21:99–102 (1989).

Rogers et al., "Complement Activation by β–amyloid in Alzheimer's Disease" *Proc. Natl. Acad. Sci. USA* 89:10016–10020 (1992).

Selkoe et al., "Isolation of Low–Molecular–Weight Proteins From Amyloid Plaque Fibers In Alzheimer's Disease" *J. Neurochem.* 46:1820–1834 (1986).

Shen and Murphy, "Solvent Effects on Self–Assembly of β–Amyloid Peptide" *Biophys. J.* 69:640–651 (1995).

Snow et al., "The Presence of Heparan Sulfate Proteoglycans in the Neuritic Plaques and Congophilic Angiopathy in Alzheimer's Disease" *Am. J. Pathol.* 133:456–463 (1988).

Snyder et al., "Amyloid–β Aggregation: Selective Inhibition of Aggregation In Mixtures of Amyloid With Different Chain Lengths" *Biophys. J.* 67:1216–1228 (1994).

Soreghan et al., "Surfactant Properties of Alzheimer's Aβ Peptides and the Mechanism of Amyloid Aggregation" *J. Biol. Chem.* 269:28551–28554 (1994).

Stevens et al., "A Molecular for Self–Assembly of Amyloid Fibrils: Immunoglobulin Light Chains" *Biochemistry* 34:10697–10702 (1995).

Stine et al., "The Nanometer–Scale Structure of Amyloid–β Visualized By Atomic Force Microscopy" *J. Protein Chem.* 15:193–203 (1996).

Strittmatter et al., "Binding of Human Apolipoprotein E to Synthetic Amyloid β Peptide: Isoform–specific Effects and Implications For Late–Onset Alzheimer Disease" *Proc. Natl. Acad. Sci. USA* 90:8098–8102 (1993).

Wisniewski and Franglone "Apolipoprotein E: A Pathological Chaperone Protein In Patients With Cerebral and Systemic Amyloid" *Neurosci. Lett.* 135:235–238 (1992).

Zagorski and Barrow, "NMR Studies of Amyloid β–Peptides: Proton Assignments, Secondary Structure, and Mechanism of an α–Helix β–Sheet Conversion For A Monologous, 28–Residue, N–Terminal Fragment" *Biochemistry* 31:5621–5631 (1992).

Lazar et al., *Mol. Cell. Biology* B:1247–1252 (1988).

Burgess et al., *J. Cell. Biol.* 111:2129–2138 (1990).

Hilbich et al., J. Mol. Biol. 218:149j–163 (1991).

Desmadril et al., Proteins 10(4):315–342 (1991).

SEQUENCE LISTING

<160> NUMBER OF SEQ ID NOS: 2

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42

```
<212> TYPE: PRT
<213> ORGANISM: Homo sapiens

<400> SEQUENCE: 2

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40
```

FLUORESCENT AMYLOID Aβ PEPTIDES AND USES THEREOF

CROSS REFERENCE TO RELATED APPLICATIONS

This application is a divisional and claims priority from utility application Ser. No. 09/133,866, filed Aug. 13, 1998 now U.S. Pat. No. 6,600,017 and claims benefit from provisional application No. 60/055,660 filed on Aug. 14, 1997, each of which is hereby incorporated by reference.

STATEMENT AS TO FEDERALLY SPONSORED RESEARCH

This invention was made with Government support under Grant No. NS31230, awarded by the National Institutes of Health. The Government has certain rights in this invention.

BACKGROUND OF THE INVENTION

In general, the invention features fluorescent Aβ peptides and methods for their use.

The extracellular deposition of β-amyloid in senile plaques is one of the neuropathological hallmarks of Alzheimer disease (AD). The major constitutive component of amyloid plaques is the Aβ peptide, a 39 to 43 residue polypeptide (Selkoe et al., (1986) *J. Neurochem.* 46:1820-1834) that is proteolytically derived from the amyloid precursor protein (APP), a much larger type I transmembrane protein. Aβ is folded into the β-sheet structure that is characteristic of amyloid fibrils.

Amyloid plaque formation likely involves two basic steps: the initial formation of a seeding aggregate that establishes the amyloid fibril lattice (Kirschner et al., (1987) *Proc. Natl. Acad. Sci. USA* 84:6953-6957), followed by the elongation of the fibril by the sequential addition of subunits (Maggio et al., (1992) *Proc. Natl. Acad. Sci. USA* 89:5462-5466). Some of the key parameters that promote the assembly of amyloid fibril include high peptide concentration, long incubation time, low pH (pH 5-6) (Barrow et al., (1991) *Science* 253:179-182; Burdick et al., (1992) *J. Biol. Chem.* 267:546-554; and Fraser et al., (1991) *Biophys. J.* 60:1190-1201), solvent composition (Shen and Murphy, (1995) *Biophisical J.* 69:640-651), and salt concentration (Hilbich et al., (1991) *J. Mol. Biol.* 218:149-163). Assembly of Aβ into the fibrils may also be promoted by molecules that interact with Aβ and increase its rate of aggregation in vitro including ApoE (Strittmatter et al., (1993) *Proc. Natl. Acad. Sci. USA* 90:8098-8102; and Wisniewski and Frangione, (1992) *Neurosci. Lett.* 135:235-238), α1-antichymotrypsin (Abraham et al., (1988) *Cell* 52:487-501), complement C1q (Rogers et al., (1992) *Proc. Natl. Acad. Sci. U.S.A.* 89:10016-10020), heparin sulfate proteoglycan (Snow et al., (1988) *Am. J. Pathol.* 133:456-463), and zinc ions (Bush et al., (1994) *J. Biol. Chem.* 269:2152-12158; and Bush et al., (1994) *Science* 265:1464-1467).

Although many of the parameters influencing fibril assembly have been elucidated, relatively little is known about the structure of soluble Aβ. Gel filtration analysis of Aβ in solution reveals the presence of multiple, discrete structures that have variously been interpreted as monomer, dimer, trimer, and higher order aggregates (Barrow et al., (1992) *J. Mol. Biol.* 225:1075-1093; Bush et al., (1994) *J. Biol. Chem.* 269:2152-12158; Hilbich et al., (1991) *J. Mol. Biol.* 218:149-163; Soreghan et al., (1994) *J. Biol. Chem.* 269:28551-28554; and Zagorski and Barrow, (1992) *Biochemistry* 31:5621-5631). The oligomeric structure depends on the concentration of the peptide, time of incubation, and the length of its carboxyl terminus (Soreghan et al., (1994) *J. Biol. Chem.* 269:28551-28554).

SUMMARY OF THE INVENTION

In general, the invention features a composition that includes an aggregating amyloid Aβ peptide to which is covalently bonded a fluorescent label. In one preferred embodiment, the fluorescent label is covalently bonded to a cysteine amino acid. The invention also features a method for generating such a preferred aggregating amyloid Aβ peptide. The method involves (a) generating an amyloid Aβ peptide including a cysteine amino acid substitution; (b) covalently bonding a fluorescent label to the peptide at the cysteine amino acid; and (c) determining whether the peptide is capable of aggregating with another Aβ peptide.

In other preferred embodiments, the wild type amyloid Aβ peptide is a human Aβ peptide; the amyloid Aβ peptide has the amino acid sequence of SEQ ID NO: 1 or SEQ ID NO: 2; the cysteine amino acid of the peptide replaces an amino acid in a wild type Aβ peptide and, for example, replaces an internal amino acid or a hydrophobic amino acid of the peptide. Preferred aggregating Aβ peptides include, without limitation, those having the sequence of SEQ ID NO: 1 or SEQ ID NO: 2, except that a cysteine replaces either a phenylalanine at position 4, an aspartic acid at position 7, a glycine at position 25, or a leucine at position 34. Preferred fluorescent labels include any thiol-reactive fluorescent dyes (for example, 5-(2-((iodoacetyl)amino)ethyl) aminonapthylene-1-sulfonic acid (1,5-IEDANS) or fluorescein) or any of the light-emitting moieties chosen from the group consisting of dipyrromethane boron fluoride (Bodipy), fluorescent thiosemicarbazide (FTC), sulforhodamine 101 acid chloride (Texas Red), phycoerythrin, rhodamine, carboxytetramethylrhodamine, 4,6-diamino-2-phenylindole (DAPI), an indopyras dye, pvrenyloxytrisulfonic acid (Cascade Blue), 514 carboxylic acid (Oregon Green), eosin, erythrosin, pyridyloxazole, benzoxadiazole, aminonapthalene, pyrene, maleimide, a coumarin, 4-fluoro-7-nitrobenzofurazan (NBD), 4-amino-N-[3-(vinylsulfonyl)-phenyl]napthalimide-3,6-disulfonate) (Lucifer Yellow), propidium iodide, a porphyrin, a cyanine dye ($CY^3$, $CY^5$, $CY^9$), a lanthanide chelate, a derivative thereof, and an analog thereof.

The aggregating Aβ peptides of the invention are useful in methods for detecting or monitoring Aβ production, accumulation, aggregation, or disaggregation. One particular method for the detection of an amyloid aggregate (for example, an amyloid plaque) involves (a) contacting the sample with an aggregating amyloid Aβ peptide to which is covalently bonded a fluorescent label; and (b) detecting the fluorescent label in association with the sample as an indication of an amyloid aggregate.

In preferred embodiments, this method is carried out to diagnose Alzheimer's disease or a predisposition thereto; the fluorescent label is covalently bonded to a cysteine amino acid; the cysteine amino acid replaces an amino acid in a wild type Aβ peptide; the cysteine amino acid replaces a hydrophobic amino acid or an internal amino acid in a wild type amyloid Aβ peptide; the aggregating Aβ peptide is chosen, without limitation, from peptides having the sequence of SEQ ID NO: 1 or SEQ ID NO: 2, except that a cysteine replaces either a phenylalanine at position 4, an aspartic acid at position 7, a glycine at position 25, or a leucine at position 34; and the fluorescent label is a thiol-reactive fluorescent dye (for example, 5-(2-((iodoacetyl)

amino)ethyl) aminonapthviene-1-sulfonic acid (1,5-IEDANS) or fluorescein) or is chosen from the light-emitting moieties, dipyrromethene boron fluoride (Bodipy), fluorescein thiosemicarbazide (FTC), sulforhodamine 101 acid chloride (Texas Red), phycoerythrin rhodamine, carboxytetramethylrhodamine, 4,6diamino-2-phenylifldole (DAPI), an indopyras dye, pyrenyloxytrisulfonic acid (Cascade Blue, 514 carboxylic (Oregon Green), eosin, erythrosin, pyridyloxazole, benzoxadiazole, aminonapthalene, pyrene, maleimide, a coumarin, 4-fluoro-7-nitrobenfurazan (NBD), 4-amino-N[3-(vinylsulfonyl)-(phenyl]napthalimide-3,6-disulfonate) (Lucifer Yellow, propidium iodide, a porphyrin, a cyanine dye ($CY^3$, $CY^5$, $CY^9$, a lanthanide cryptate, a lanthanide chelate, or a derivative or analog thereof.

The aggregating Aβ peptides of the invention also find use in screens for identifying compounds capable of affecting the aggregation of Aβ amyloid peptide. One particular method involves (a) providing a sample of Aβ amyloid peptide; (b) contacting the sample with (i) an aggregating amyloid Aβ peptide to which is covalently bonded a fluorescent label; and (ii) a candidate compound; and (c) measuring association of the fluorescent label with the sample, a change in the level of fluorescent label found in association with the sample relative to a control sample lacking the candidate compound being an indication that the compound is capable of affecting Aβ amyloid peptide aggregation. In a preferred embodiment of this method, the sample includes unlabeled Aβ amyloid peptide bound to a solid support, and the aggregation is measured by association of the fluorescent label with the solid support.

The invention also includes a second exemplary method for identifying a compound capable of affecting the aggregation of Aβ amyloid peptide. This method involves (a) providing a sample of an aggregating amyloid Aβ peptide to which is covalently bonded a fluorescent label; (b) contacting the sample with a candidate compound; and (c) measuring the ability of the peptide to aggregate, a change in the amount of aggregated peptide in the presence of the candidate compound relative to a sample lacking the compound being an indication that the compound is capable of affecting Aβ amyloid peptide aggregation.

In preferred embodiments of both of the above screening methods, the fluorescent label is covalently bonded to a cysteine amino acid; the cysteine amino acid replaces an amino acid in a wild type Aγ peptide; the cysteine amino acid replaces a hydrophobic amino acid or an internal amino acid in a wild type amyloid Aβ peptide; the aggregating Aβ peptide is chosen, without limitation, from peptides having the sequence of SEQ ID NO: 1 or SEQ ID NO: 2, except that a cysteine replaces either a phenylalanine at position 4, an aspartic acid at position 7, a glycine at position 25, or a leucine at position 34; the fluorescent label is a thiol-reactive fluorescent dye (for example, 5-(2-((iodoacetvI)amino) ethyl) aminoaothylene-1-sulfonic acid (1,5-IEDANSI or fluorescein) or is chosen from the group of Light-emitting moieties consisting of diopyrromethene boron fluoride (Bodipyl, fluorescein thiosemicarbazide (FTC), sulforhodamine 101 acid chloride (Texas Red), phycoerythrin, rhodamine, carboxytetramethylrodamine, 4,6-diamino-2-phenylindole (DAPI), an indopyras dye, pyrenyloxytrisulfonic acid (Cascade Blue), 514 carboxylic acid (Oregon Greeni, eosin, erythrosin, pyridyloxazole, benzoxadiazole, aminonapthalene, pyrene, maleimide, a coumarin, 4-fluoro-7-nitrobenzofurazan (NBD), 4-amino-N-[3-(vinylsulfonyl)-phenyl]napthalimide-3,6-disulfonate) (Lucifer Yellow), propidium iodide, a porphyrin a cyanine dye ($CY^3$, $CY_5$, $CY^9$, a lanthanide cryptate, a lanthanide chelate, a derivative thereof, and an analog thereof; and aggregation is measured by centrifugation, gel filtration, or fluorescence resonance energy transfer (FRET) analysis.

As used herein, by an "amyloid Aβ peptide" is meant any β-amyloid peptide or fragment thereof which aggregates under physiological conditions (for example, as tested herein).

By a "wild type" Aβ peptide is meant any naturally occurring β-amyloid peptide.

By an "aggregating" amyloid Aβ peptide is meant that, under physiological conditions, the peptide (which is fluorescently labeled) exhibits at least 70%, preferably at least 80%, more preferably at least 90%, and most preferably at least 95% of the aggregate formation exhibited by a corresponding unlabeled peptide under identical conditions.

By an "internal amino acid" is meant any amino acid of a peptide except the amino-terminal or carboxy-terminal residues.

The present invention provides a number of advantages. Most notably, because the peptides described herein represent the first examples of fluorescently labeled Aβ peptides that exhibit wild type aggregation properties, this invention enables any number of diagnostic techniques that appropriately monitor amyloid aggregation or disaggregation. In addition, also because of the peptides' wild type aggregation characteristics, the invention enables, for the first time, screening techniques using biologically relevant fluorescent Aβ peptides for the discovery of compounds that affect amyloid peptide aggregation. Such compounds provide important candidate therapeutics, for example, for the treatment or amelioration of Alzheimer's disease or its symptoms.

Other features and advantages of the claimed invention will be apparent from the following detailed description thereof, and from the claims.

DETAILED DESCRIPTION OF THE INVENTION

The drawings will first briefly be described.

BRIEF DESCRIPTION OF THE DRAWINGS

In FIG. 2A, chromatogram "a" shows the elution profile of wild type Aβ as detected by absorbance at 280 nm. Chromatograms "b" and "c" show the elution of AβC25-AEDANS and AβC7-FM, respectively, as detected by fluorescence at 482 nm and 520 nm, respectively. The peptides were dissolved in DMSO for 30 minutes and then ten fold diluted in buffer A at a final protein concentration of 5-10 µM. A 200 µl aliquot was loaded onto a Superdex 75HR 10/30 column and eluted at a rate of 0.4 ml/min. The inset in the upper left corner shows the calibration curve for the column using a series of peptide and protein standards as described below. FIG. 2B shows the elution profile of 2.0 nM Aβ$^{14}$C Aβ run under the same conditions above and detected by scintillation counting.

FIG. 5A shows an emission spectrum of an equal molar amount of AβC25-AEDANS (donor) and AβC7-FM (acceptor) mixed in DMSO and then diluted 10-fold in Buffer A (• • • •). The final protein concentration was 3 μM. The control spectrum (—) corresponds to the mathematical sum of the following control samples: an equal molar mixture of AβC25-AEDANS and Aβ and an equal molar mixture of AβC7-FM and Aβ. Efficient FRET is evident by the quenching of the donor and an increased emission of the acceptor. FIG. 5B shows the emission spectrum for the other donor-acceptor pair, AβC34-AEDANS and AβC4-FM. FIG. 5C shows the emission spectrum of the mixture of AβC25-AEDANS, AβC 7-FM plus a 10-fold molar excess of wild type Aβ(—). The control spectrum (—) corresponds to the arithmetical sum of the controls for donor alone and acceptor alone in the presence of 10 fold excess of wild type peptide. The addition of an excess of unlabeled Aβ abolished the FRET between AβC25-AEDANS and AβC7-FM.

FIGS. 6A and 6C represent the steady-state emission data, and FIGS. 6B and 6D represent the corresponding deconvoluted spectra. The traces correspond to the emission spectra of the mixture of Aβ and AβY10W (spectrum 1), and the following controls: donor Aβ alone (spectrum 2) and acceptor AβY10W alone (Barrow et al., (1991) *Science* 253:179-182). Spectrum 4 represents the mathematical sum of spectra 2 and 3. Spectrum 5 represents the deconvoluted emission spectra of the acceptor in the mixture and is obtained by multiplying spectrum 3 by the factor ($F_{DA}/F_A$), where $F_{DA}$ is the emission of the acceptor in the mixture and $F_A$ is the emission of the acceptor alone. Spectrum 6 is the deconvoluted emission spectrum of the donor in the mixture and is obtained by subtraction of spectrum 5 from spectrum 1. The Aβ concentration was 10 μM. The association of Aβ and AβY10W is more readily evident in the deconvoluted spectra in FIGS. 6B and 6D, as indicated by the quenching of the donor tyrosine and an increase in the emission of the acceptor tryptophan.

Described below are exemplary amyloid Aβ peptides according to the invention. These peptides are fluorescently labeled and exhibit the aggregation properties of wild type Aβ peptides. Because of these properties, the peptides described herein find use in diagnostic methods for Alzheimer's disease that involve detection of amyloid plaques by aggregation with the fluorescent Aβ peptides described herein. The ability of these peptides to aggregate in a fashion similar to wild type Aβ also enables the design of assays to screen for compounds capable of disrupting fluorescent Aβ or fluorescent Aβ-wild type Aβ aggregates. Finally, the fluorescent Aβ peptides described herein may be used as detection reagents in any standard fluorescence anisotropy or fluorescence polarization technique.

The following examples are provided for the purpose of illustrating the invention, and should not be construed as limiting.

EXAMPLE 1

Synthesis and Characterization of Fluorescent Aβ Peptides

The Aβ peptides of the invention were chemically synthesized, fluorescently labeled, and characterized as follows.

Synthesis and Aggregation Properties of Fluorescent Aβ Peptides

A series of Aβ variants containing a single cysteine substitution were chemically synthesized as described below. Cysteine was chosen because of its unique chemical reactivity and its absence in the wild type Aβ sequence (SEQ ID NO: 1). Initially, a series of cysteine substitutions were synthesized by replacing every third residue because the cysteine side chain was expected to alternate on opposite sides of the strand in a beta sheet structure. The cysteine-containing probe peptides were covalently labeled with a variety of extrinsic fluorescent probes. Mass spectrometry confirmed the expected mass of the final product, and the absence of the precursor peptide indicated that the labeling reaction was complete. A peptide containing tryptophan instead of tyrosine at position 10 was also synthesized to use as an acceptor for intrinsic tyrosine fluorescence of the wild type peptide.

Figure 1:
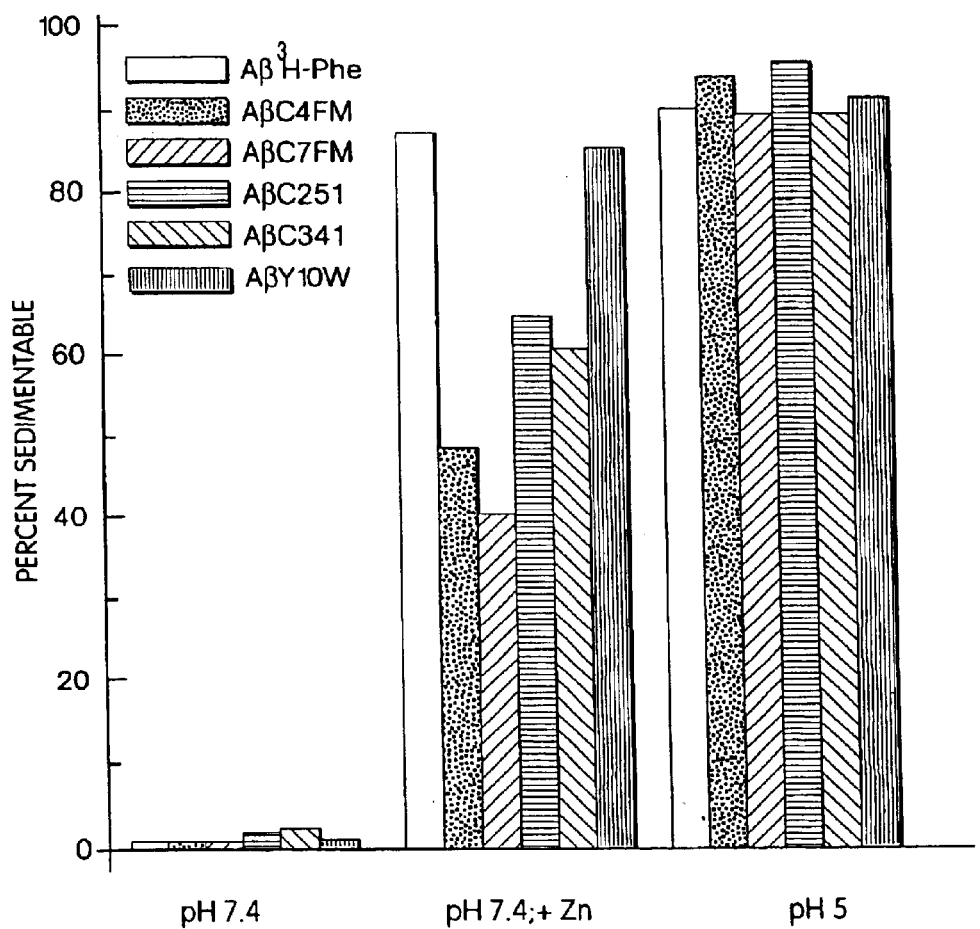
FIG. 1 is a bar graph illustrating the aggregation properties of fluorescent derivatives of Aβ. The aggregation properties of the fluorescent derivatives were compared with wild type Aβ under physiological conditions where the wild type peptide was largely soluble (i.e., Tris buffered saline at pH 7.4) and under two additional conditions known to promote fibrillization: pH 5.0 and at pH 7.4 in the presence of 70 µM $Zn^{++}$ (as described below). The samples were centrifugated after a 48 hour incubation. The amount of sedimentable wild type peptide was determined by scintillation counting, and the amount of sedimentable fluorescent peptide was determined by fluorescence intensity.
Figure 2A:
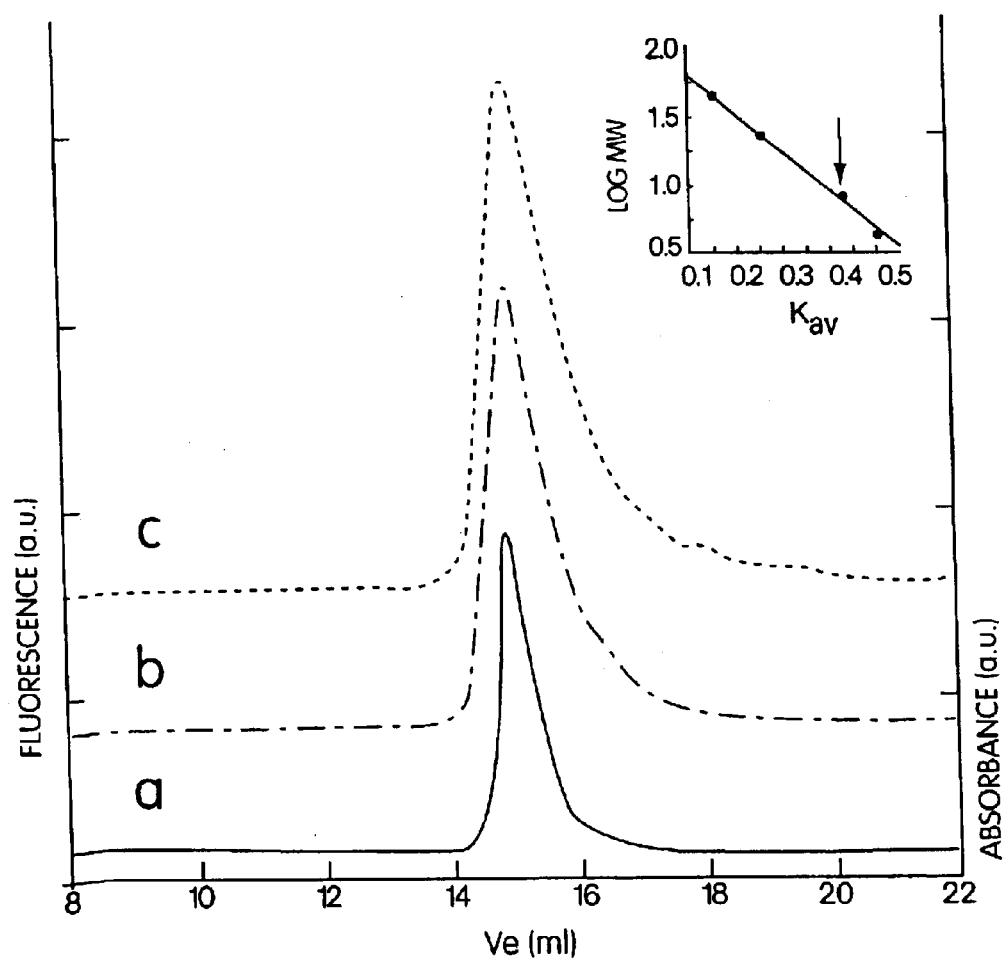
FIGS. 2A-2B are graphs illustrating gel filtration analyses of fluorescent Aβ.
Figure 2B:
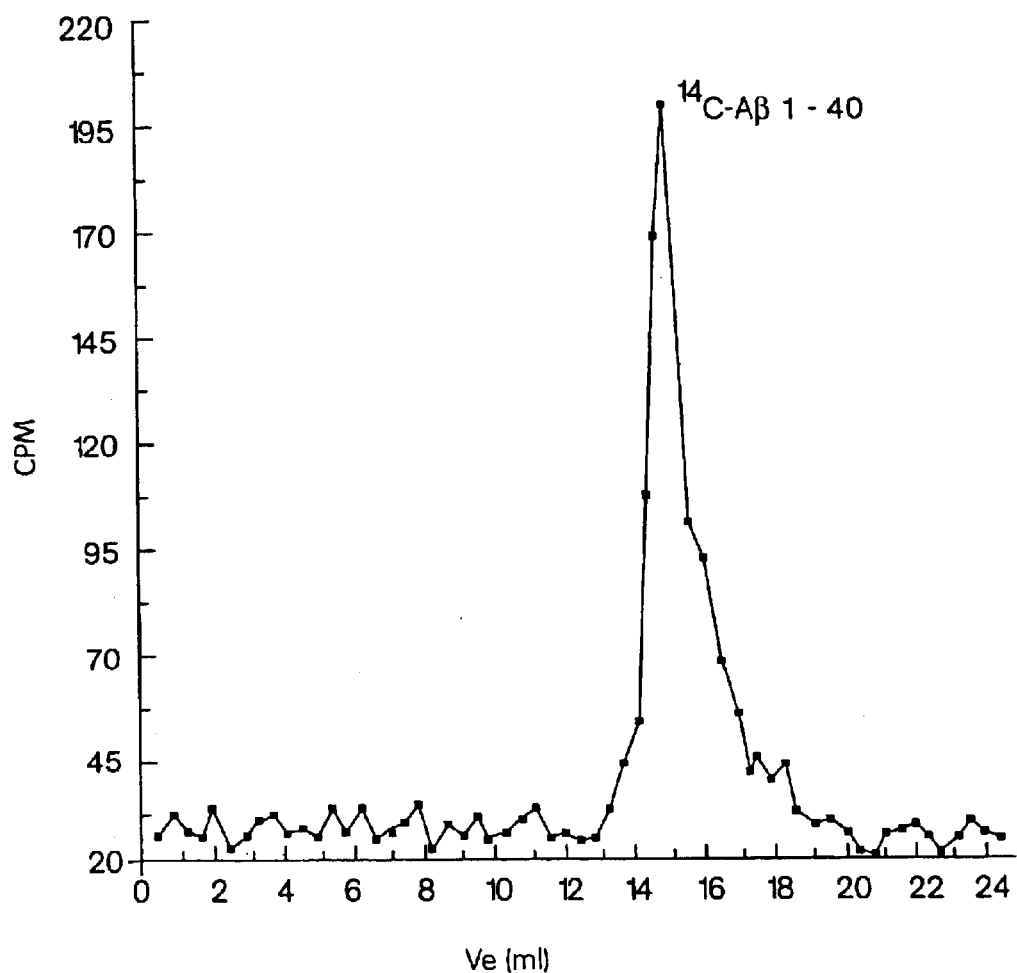

The aggregation properties of the fluorescent derivatives were compared to wild type Aβ under physiological conditions (e.g., Tris buffered saline at pH 7.4) where the peptide was largely soluble, as well as under conditions that were known to promote fibril assembly (e.g., pH 5.0 and pH 7.4 in the presence of $Zn^{++}$) (FIG. 1). As shown in FIG. 1, at pH 7.4 and at pH 5.0, all of the fluorescent peptides were indistinguishable from wild type Aβ. In the presence of 70 μM $Zn^{++}$, the fluorescein and AEDANS labeled Aβ peptides aggregated to approximately 50-75% of the extent of wild type Aβ. However trp substitution at residue 10 did not alter the aggregation behavior in response to $Zn^{++}$. The oligomeric structure of the fluorescent peptides was characterized by gel filtration, and the fluorescent peptides were found to elute at the same position as wild type Aβ (FIGS. 2A and 2B). The elution position corresponded to an apparent molecular mass of 9,000 Da established by the elution behavior of a series of calibration standards (FIG. 2A, inset). The calibration curve also indicated that the expected elution position for a peptide of the mass of monomeric Aβ was well separated from the observed elution position of Aβ. Nanomolar concentrations of $^{14}$C-labeled Aβ 1-40 also eluted at the position expected for a dimer (FIG. 2B).

Denaturation and Renaturation of Aβ in DMSO

In order to analyze the structure of soluble Aβ by fluorescence resonance energy transfer (FRET), conditions were established for the denaturation and renaturation of Aβ. Previous studies using a combination of Fourier transform infrared spectroscopy, and dynamic light scattering (Shen and Murphy, (1995) *Biophisical J.* 69:640-651; and Snyder et al., (1994) *Biophys. J.* 67:1216-1228) demonstrated that Aβ was denatured and monomeric in DMSO. The intrinsic fluorescence of proteins provides a signal commonly used to monitor conformational changes and unfolding (Wu et al., (1994) *Biochemistry* 33:7415-74222). In the present work, the intrinsic tyrosine fluorescence of wild type Aβ was used to assay the denaturation of Aβ in DMSO, and its renaturation. The tyrosine emission of most native proteins and peptides is frequently small or undetectable due to the presence of more highly fluorescent tryptophan residues (Lakowicz, (1983) *Principles of Fluorescence, Plenum Press, New York, N.Y.*; and Wu et al., (1994) *Biochemistry* 33:7415-74222), but tryptophan is absent in Aβ.

Figure 3:
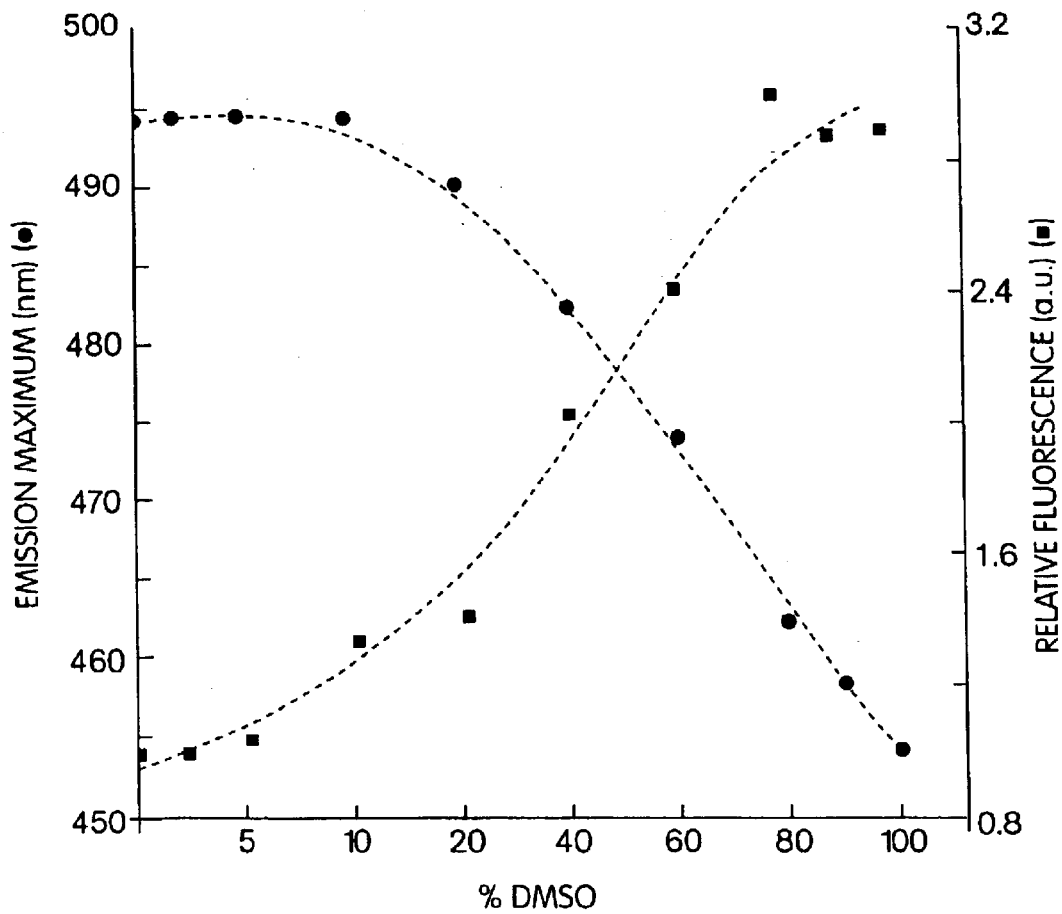
FIG. 3 is a graph illustrating the unfolding of Aβ measured by tyrosine fluorescence and 1,5-IAEDANS fluorescence. Equilibrium unfolding curves were monitored by measuring the intrinsic tyrosine fluorescence at 308 nm on excitation at 280 nm of wild type Aβ (solid squares) and AβC25-AEDANS fluorescence at excitation 346 nm (solid circles). The protein concentration was 5-10 μM of Aβ.

The denaturation curve for wild type Aβ showed a single, smooth cooperative transition (FIG. 3). Increasing concentrations of DMSO increased the intrinsic fluorescence intensity of Aβ, indicating that a significant increase in the exposure of the tyrosine residue occurred in the unfolded state. The mid-point of intrinsic fluorescence changes occurred at approximately 40% DMSO. The emission maximum of tyrosine was not affected by DMSO, remaining the same at all concentrations (i.e., 308 nm) because the tyrosine fluorescence emission maximum was not sensitive to the polarity of the solvent (Lakowicz, (1983) *Principles of Fluorescence, Plenum Press, New York, N.Y.*). The data described herein were corrected for the relatively small solvent effect of DMSO on free tyrosine to ensure that the curve accurately reflected the unfolding of Aβ.

Having determined the above parameters for wild type Aβ, the denaturation of the extrinsically-labeled fluorescent Aβ probes was also examined. For environment-sensitive fluorophores (like 1,5-IAEDANS) the emission maximum shifts to a shorter wavelength (blue shift) as the polarity of the surrounding environment decreases (Lakowicz, (1983) *Principles of Fluorescence, Plenum Press, New York, N.Y.*). Conversely the emission maximum shifts to the longer wavelengths (red shift) in a more polar environment. For AβC25-AEDANS, a marked blue-shift (42 nm) of the emission was observed upon unfolding by DMSO (FIG. 3), indicating that the fluorophore was increasingly exposed to the surrounding media at increasing DMSO concentrations. As with the intrinsic tyrosine fluorescence, the midpoint of the blue shift of AEDANS occurred at approximately 50% DMSO. The unfolding transition was complete within 2 hours, and identical unfolding curves were obtained for the other fluorescent-labeled AB peptides, AβC4FM, AβC34AEDANS, and AβC7FM. At concentrations of DMSO below 10%, there was little further change in the intrinsic fluorescence emission of Aβ or the extrinsic fluorescence of AβC25-AEDANS (FIG. 3). These results indicated that AEDANS-labeled and wild type Aβ peptides had similar stabilities and suggested that there was relatively little change in the overall structure of Aβ over the range of DMSO from 0%-10%.

Figure 4A:
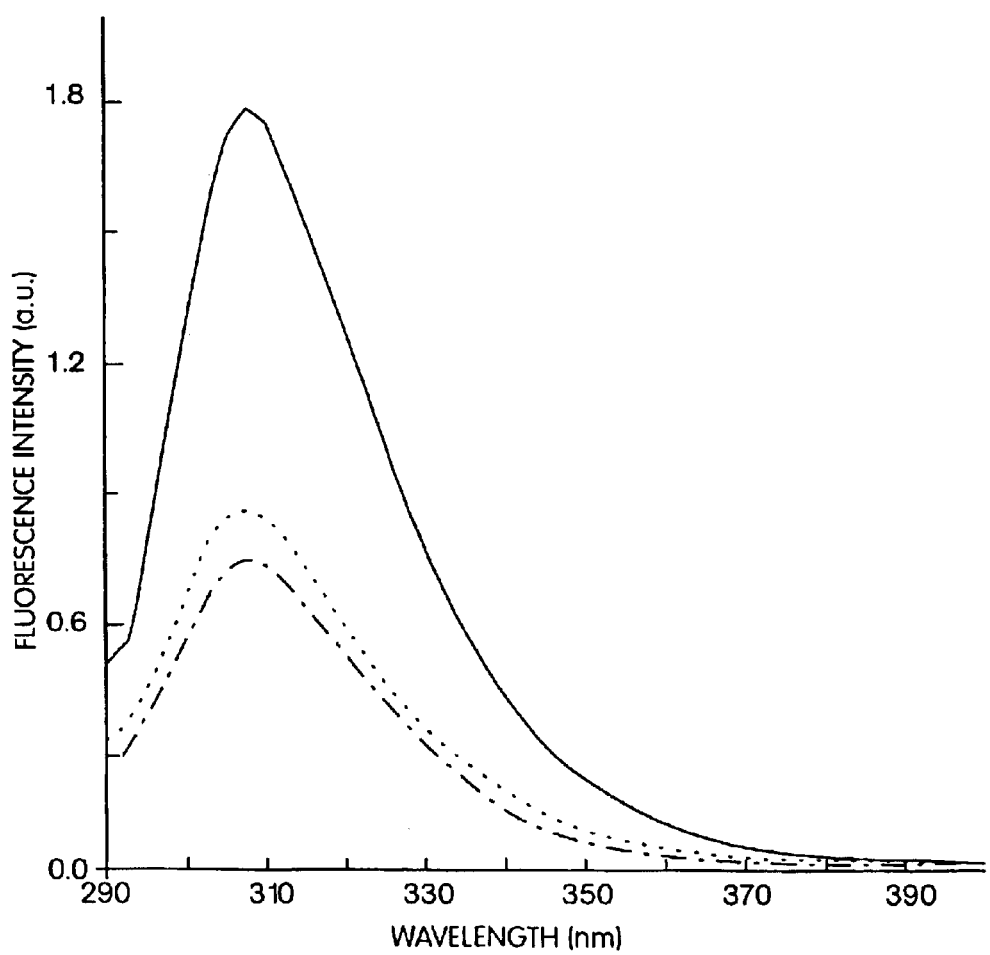
FIGS. 4A and 4B are graphs illustrating the renaturation of Aβ measured by tyrosine fluorescence and AEDANS fluorescence. The emission spectra of either peptide freshly dissolved in buffer A (-•-•-), peptide dissolved in 100% DMSO (—), or peptide dissolved in 100% DMSO and then diluted 10-fold in buffer A (• • • •) are shown. The wild type peptide is presented in FIG. 4A, and AβC25-AEDANS is presented in FIG. 4B. Emission spectra were recorded from 290 to 400 nm with an excitation at 280 nm for tyrosine fluorescence and 356 to 600 nm with an excitation at 336 nm for AβC25-AEDANS.
Figure 4B:
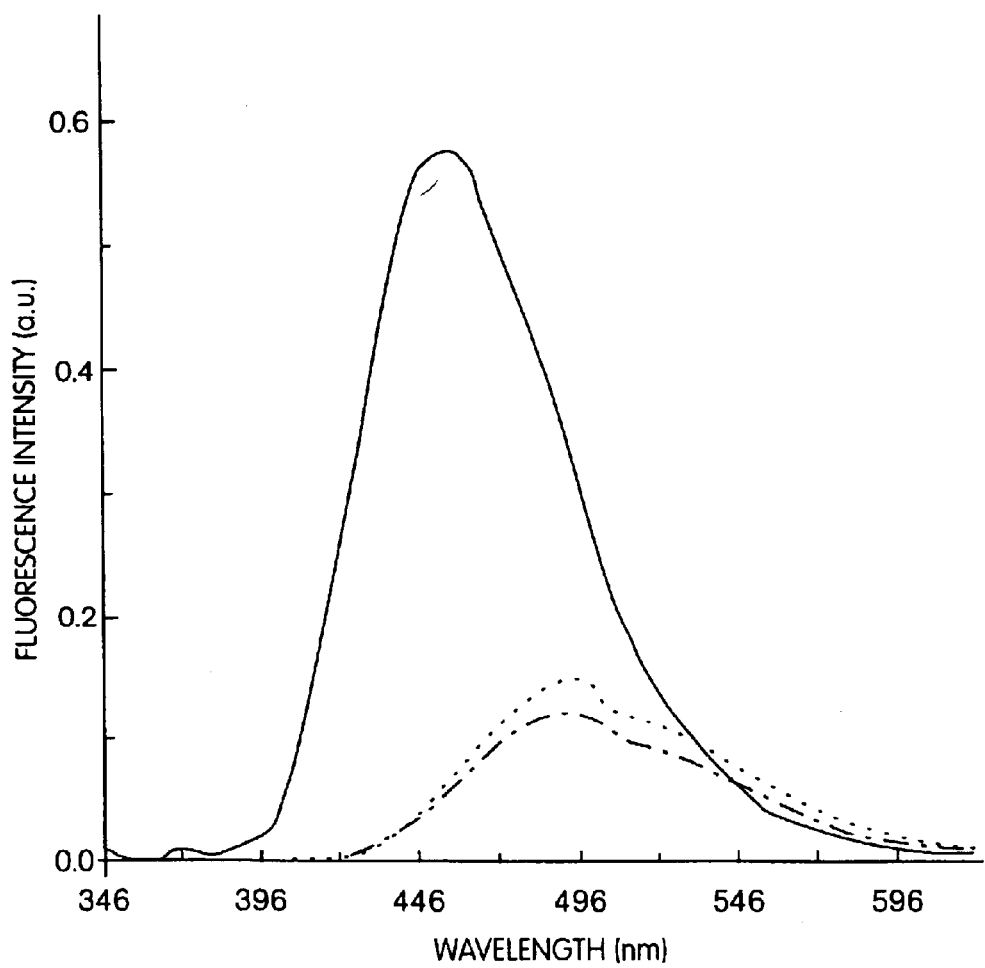

The renaturation of Aβ from DMSO solution was also examined. Upon 10-fold dilution of DMSO into aqueous buffer solution, the emission spectrum of wild type Aβ and Aβ labeled with 1,5-IAEDANS (AEDANS-AβC25) showed the same maximum at 308 nm and 494 nm as observed for the peptides dissolved directly in Buffer A, indicating that the denatured peptide returned to the same overall structure (FIGS. 4A and 4B). Time course studies indicated that the refolding of the peptide was immediate. When the DMSO was diluted 50-fold (2% DMSO), the emission spectrum of the refolded peptide was indistinguishable from the emission spectrum of the Aβ dissolved directly in aqueous buffer, suggesting that the denatured peptide recovered the same structure. Both samples in 10% and 2% DMSO displayed the same elution time by gel filtration. Similar denaturation and renaturation results were obtained with guanidinium hydrochloride (GdnHCl). DMSO stock solutions of peptide were employed for all of the subsequent experiments.

Association of Fluorescent Aβ Peptides

Figure 5A:
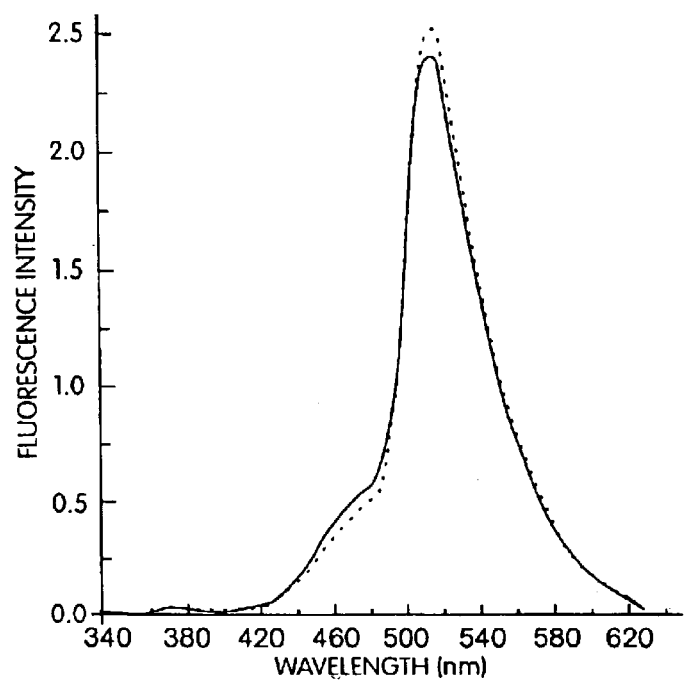
FIGS. 5A-5C are graphs illustrating the association of AEDANS-labeled and FM-labeled Aβ in dilute aqueous solution as determined by FRET.

Fluorescence resonance energy transfer between AEDANS and fluorescein was used initially to monitor association of Aβ monomers following dilution of DMSO into aqueous buffer solution. For these experiments, AβC25-AEDANS and AβC7-FM DMSO stock solutions were mixed 1:1 (donor:acceptor), and subsequently ten fold diluted in Buffer A. The final concentration of the peptide was 3 μM. The resulting fluorescence spectra are shown in FIG. 5A. Efficient FRET was observed, as evidenced by a quenching of the donor emission at 474 nm and an increase in the acceptor fluorescence at 520 nm, compared to the control spectra, indicating that hybrid Aβ dimers had formed in the mixture containing both donor and acceptor (FIG. 5A). The efficiency of FRET did not change significantly upon subsequent incubation for 24 hours.

In order to control for possible effects of peptide structure on the fluorescence intensity of labeled peptides, control measurements were carried out in which either AβC25-AEDANS or AβC7 FM were individually mixed with an equal amount of non-labeled peptide in DMSO, and then diluted 10-fold in Buffer A. The emission spectra obtained for AβC25-AEDANS or AβC7 FM are shown as arithmetic sums of the individual spectra (i.e., the expected emission in the absence of energy transfer). Efficient FRET was also observed with several other pairs of Aβ peptides (Table I).

Figure 5B:
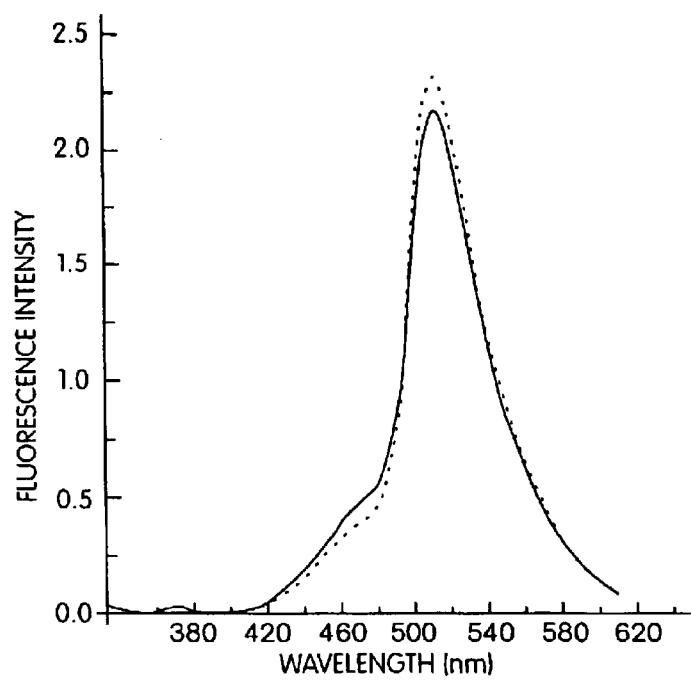

FIG. 5B shows the spectra of the energy transfer experiment where another donor-acceptor pair, AβC34-AEDANS—AβC4-FM, was used. The efficiency of FRET for this combination was higher than that observed for AβC25 AEDANS and AβC7 FM, suggesting that the peptide structure was ordered and that the fluorophores at positions 34 and 4 may be in closer proximity in the structure than those at positions 25 and 7. Once formed, the Aβ dimers appeared to be relatively stable in solution. If fluorescent homodimers were formed first by individually diluting stock solution 10-fold into Buffer A, and then subsequently mixed, no resonance energy transfer was observed over an incubation of 24 hours, indicating that subunit exchange between homodimers was not detectable over this period.

Figure 5C:
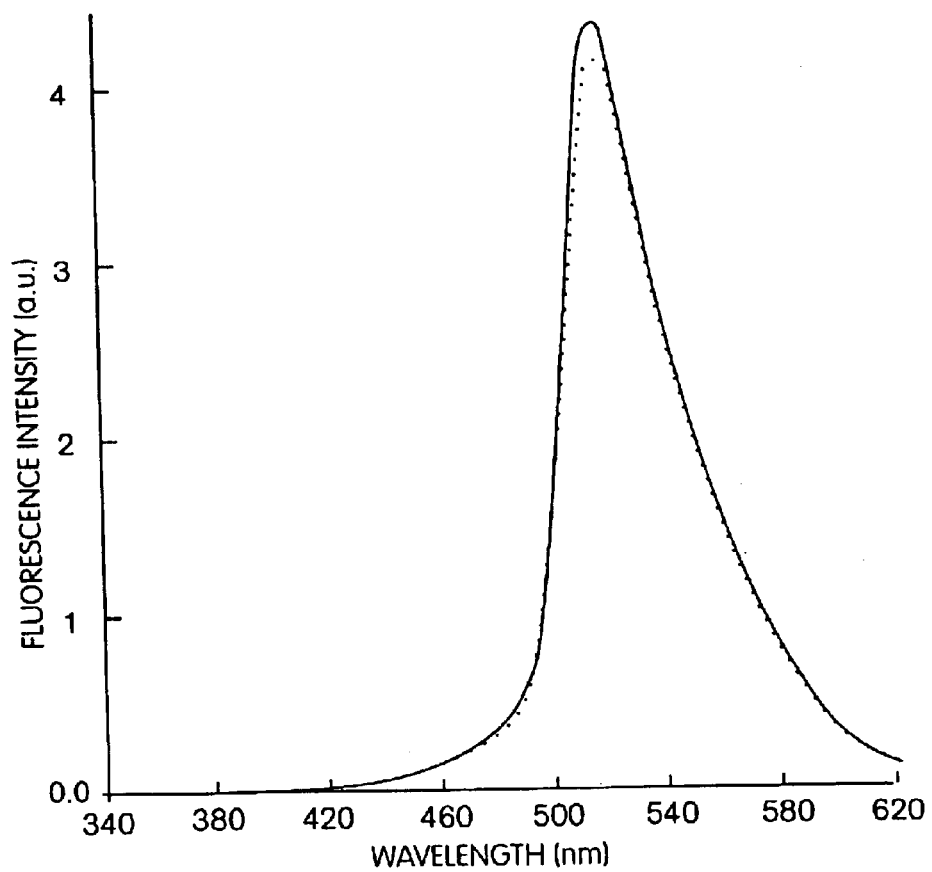
Figure 6A:
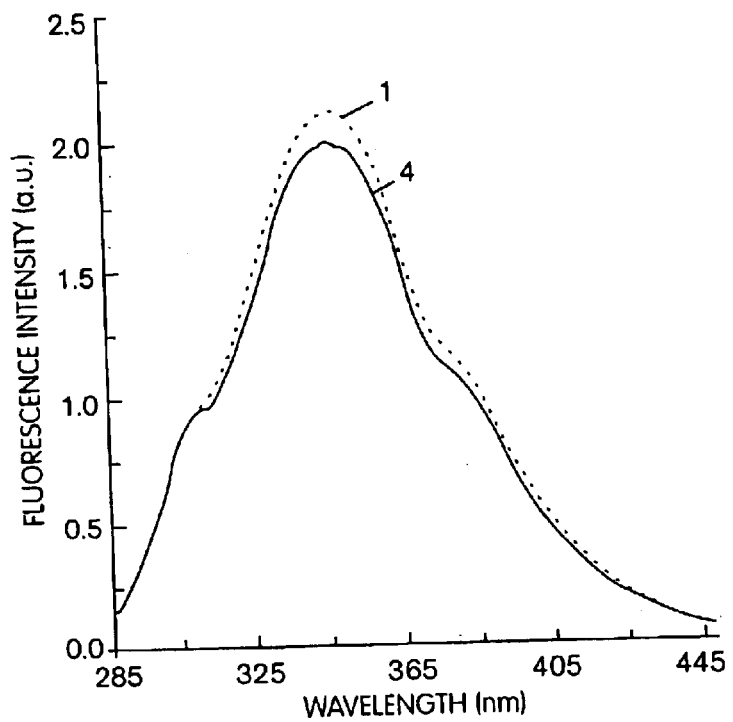
FIGS. 6A-6D are graphs illustrating the association of Aβ-AβY10W in dilute aqueous solution as determined by FRET. The association of Aβ and AβY10W in 10% DMSO in Buffer A is shown in FIGS. 6A and 6B, and the association of these same peptides in 2% DMSO in Buffer A is shown in FIGS. 6C and 6D.
Figure 6B:
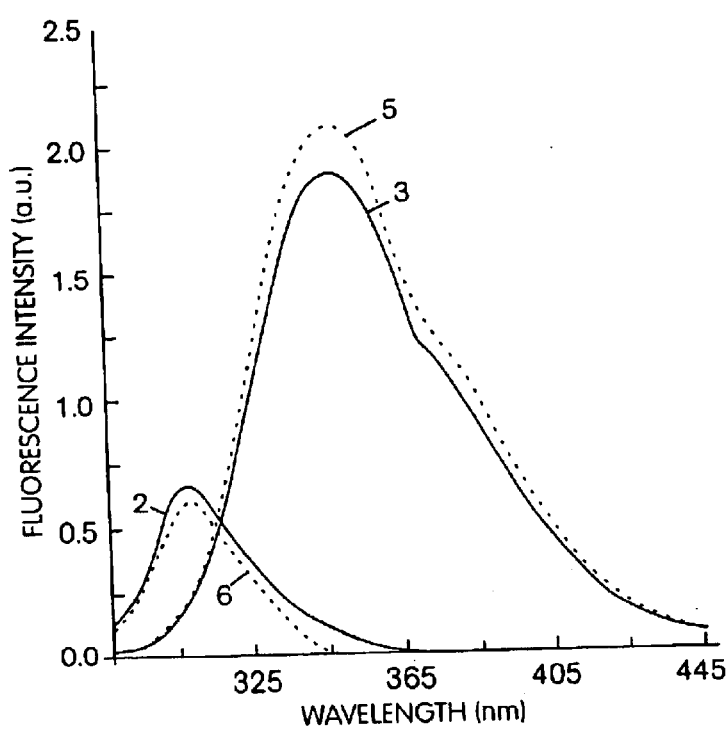
Figure 6C:
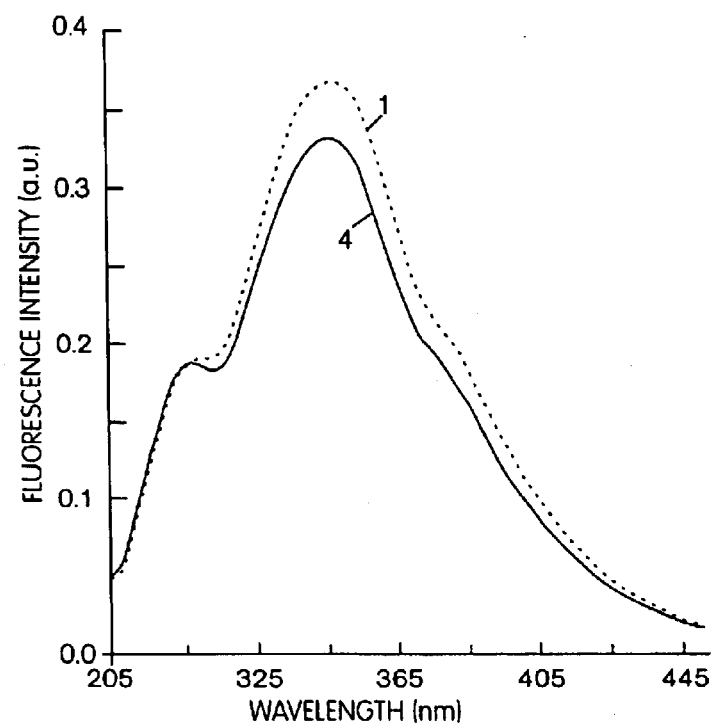
Figure 6D:
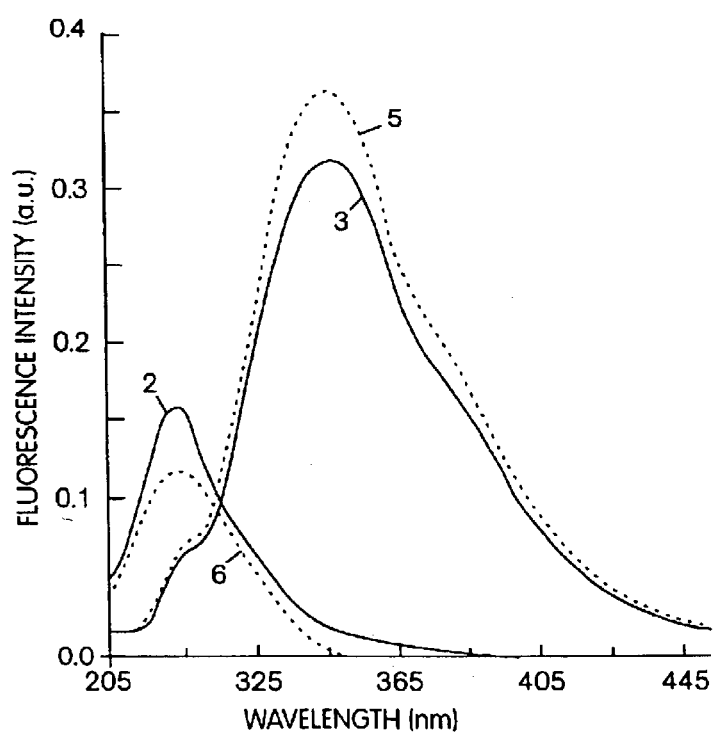

Several controls were conducted to ensure that the FRET observed was due to interactions between peptides that occurred in solution with wild type Aβ. After each FRET experiment, we confirmed that the fluorescent peptide mixture eluted at the same apparent dimer position as the wild type peptide by gel filtration chromatography. It was also determined that FRET was nearly abolished when a 10-fold molar excess of wild type peptide was added to the fluorescent peptide mixture in DMSO and then subsequently diluted (FIG. 5C), indicating that the wild type peptide could compete for the fluorescent peptides and form fluorescent and wild type Aβ heterodimers that did not exhibit FRET. Lastly, the endogenous tyrosine fluorescence of wild type Aβ was exploited as a donor for Aβ in which tryptophan replaced the tyrosine at position 10 (AβY10W).

Efficient FRET was also observed for the mixture of Aβ and AβY10W (FIG. 6). This experiment was conducted under two different conditions: (i) where the mixture was diluted to 10% DMSO (FIGS. 6A and 6B) and (ii) where the mixture was diluted to 2% DMSO (FIGS. 6C and 6D). A deconvolution analysis of FRET between Aβ and AβY10W was conducted as reported (Soreghan et al., (1994) *J. Biol. Chem.* 269:28551-28554) (FIGS. 6B and 6D). As shown in Table 1, the efficiency of FRET was found to be significantly higher in 2% DMSO than in 10% DMSO, suggesting that the structure in 10% DMSO might be partially unfolded.

TABLE 1

Efficiencies of Energy Transfer for Different Donor-Acceptor Pairs

| Donor-Acceptor pair | E (efficiency of energy transfer) | % DMSO |
|---|---|---|
| AβC25I-AβC7FM | 0.14 | 10 |
| AβC34I-AβC4FM | 0.20 | 10 |
| Aβ-AβY10W | 0.21 | 10 |
| Aβ-AβY10W | 0.46 | 2 |

Our experiments with three different donor-acceptor pairs demonstrated that efficient FRET was observed when the peptides were mixed in DMSO prior to dilution in aqueous buffer, suggesting that they formed dimers in solution. It was conceivable that the aggregates might actually represent higher order structures (e.g., trimers or tetramers). We measured the lifetime of the FM-labeled Aβ by phase modulation frequency domain methods in the range 3 μM-100 nM. The fluorescence lifetime data fit to a single decay exponential that remained constant over the concentration range. This suggested that there was a single distance between the fluorophores, and that it did not change over the concentration range examined. A single distance would be expected in a population of structurally homogenous dimers, while higher order aggregates would have to be radially symmetrical to obtain a single distance. Taken together with the gel filtration data, the simplest conclusion is that Aβ exists as a stable dimer over the concentration range from nM to μM.

Additional Aggregating Aβ Peptides

In addition to the Aβ peptides described above, an extended Aβ peptide was generated having the following sequence:
D A E F R H D S G Y E V H H Q K L V F F A E D V G S N K-GAIIGLMVGGVVIA (SEQ ID NO: 2). This peptide was chemically synthesized and fluorescently labeled (as described above) at the amino acid positions described above. These fluorescent derivatives were found to form fibrils, to aggregate, and to bind cells in a manner analogous to the unlabeled wild type peptide.

Summary of Fluorescent Aβ Peptide Characteristics

In sum, the fluorescently labeled peptides described herein possess properties characteristic of wild type Aβ. In particular, the elution behavior of the fluorescent peptides on gel filtration was identical to wild type Aβ, indicating that the fluorescent peptides had the same hydrodynamic radius in solution. In addition, denaturation-renaturation experiments demonstrated that the stability of the fluorescent peptides was indistinguishable from the wild type peptide. Moreover, when the aggregation properties of the fluorescent peptides were assayed, they were found to be nearly identical to the wild type peptides. And, lastly, experiments employing several different combinations of donor and acceptor peptides, labeled at different positions, indicated that all tested peptides behaved as dimers.

The finding that Aβ formed a stable dimer in solution suggests that dimerization is the initial event in amyloid aggregation and that it represents the fundamental building block for further fibril assembly as has been previously proposed (Shen and Murphy, (1995) *Biophisical J.* 69:640-651; and Soreghan et al., (1994) *J. Biol. Chem.* 269:28551-28554). This model of amyloid assembly is very similar to the model recently proposed for immunoglobulin light chain amyloid fibrils on the basis of molecular modeling studies (Stevens et al., (1995) *Biochemistry* 34:10697-10702). In this model, the two light chains align in a parallel fashion creating a dimer with a 2-fold axis of symmetry. It seems likely that the Aβ dimer may also have the same arrangement because it behaves as if it is axially amphipathic with one end polar and the other end hydrophobic (Soreghan et al., (1994) *J. Biol. Chem.* 269:28551-28554). This implies that at least some of the dimer may be arranged in a parallel fashion, because if the dimer were arranged in a simple head to tail fashion, as has been previously proposed (Lakowicz, (1983) *Principles of Fluorescence*, Plenum Press, New York, N.Y.), the hydrophobic moment of the resulting dimer might be expected to be symmetric with respect to the ends of the dimer. Previous CD and FTIR spectroscopic studies indicate that soluble Aβ has substantial β-sheet content, suggesting that the dimer adopts a beta structure (Barrow et al., (1991) *Science* 253:179-182; Barrow et al., (1992) *J. Mol. Biol.* 225:1075-1093; Shen and Murphy, (1995) *Biophisical J.* 69:640-651; and Zagorski and Barrow, (1992) *Biochemistry* 31:5621-5631).

In the amyloid light chain model, the next step in polymerization is head to tail association of dimers related by a 90° rotation around the 2-fold axis to form a tetramer that establishes a "proamyloid" filament lattice that is capable of propagating filaments of indefinite length. Elongation of the fibril is accomplished by the stepwise addition of dimers onto the filament. This "proamyloid" filament may correspond to the "β crystallite" proposed for Aβ from fibril diffraction measurements (Inouye et al., (1993) *Biophys. J.* 64:502-19) and observed in atomic force microscopy images (Stine et al., (1996) *J. Protein Chem.* 15:193-203). In this step, the free energy contribution of individual amino acid side chains is effectively doubled because of the 2-fold symmetry of the interacting surfaces (Stevens et al., (1995) *Biochemistry* 34:10697-10702). It seem likely that Aβ is also capable of forming a similar stable tetramer. Discrete aggregate species migrating at the position expected for a tetramer have been observed by SDS PAGE in samples of Aβ1-42 (Burdick et al., (1992) *J. Biol. Chem.* 267:546-554; and Soreghan et al., (1994) *J. Biol. Chem.* 269:28551-28554). In Aβ, the formation of this SDS-resistant higher order aggregate depends on the length of the carboxyl terminus of Aβ (e.g. only Aβ1-42 and Aβ1-43), and it is also concentration dependent, occurring at approximately the critical micelle concentration defined by surface tension measurements (Soreghan et al., (1994) *J. Biol. Chem.* 269:28551-28554). These results suggest that the formation of higher order aggregates in Aβ may be mediated predominantly by hydrophobic contacts.

The formation of amyloid fibrils in the light chain model is proposed to proceed by the lateral association of the "proamyloid" filaments or subfibrils (Stevens et al., (1995) *Biochemistry* 34:10697-10702). This step corresponds mechanistically to the formation of the nucleating center proposed for Aβ (Jarrett et al., (1993) *Biochemistry* 32:4693-4697). Evidence for the existence of subfibrils has been obtained for Aβ by rapid-freeze, deep-etch electron microscopy (Miyakawa and Kuramoto, (1989) *Ann. Med.* 21:99-102) and more recently by atomic force microscopy (Stine et al., (1996) *J. Protein Chem.* 15:193-203). In the light chain model, four strands are proposed to associate in an antiparallel fashion, but it is not clear how many subfibrils are contained within Aβ fibrils. The number of subfibrils for amyloid Aβ fibrils is not clear, but electron micrographs show images that appear to contain 5 subfibrils and this number gives the best fit in modeling the observed reflections in fiber diffraction studies (Inouye et al., (1993) *Biophys. J.* 64:502-19). It is also conceivable that this number could vary within a population of Aβ fibrils and this could account for differences in the diameter and morphology of fibrils that has been reported (Stine et al., (1996) *J. Protein Chem.* 15:193-203), as well as the fact that sheet and ribbon morphologies are also known to occur in synthetic Aβ aggregates (Burdick et al., (1992) *J. Biol. Chem.* 267:546-554; and Halverson et al., (1990) *Biochemistry* 29:2639-2644). Other than the initial dimerization event, the details of this model of amyloid fibril formation remain to be verified experimentally for Aβ.

Fluorescent derivatives of A13 are also useful for exploring other aspects of amyloid structure. For example, quantitative measurements of distances between fluorescent dipoles by FRET are possible (Lakowicz, (1983) *Principles of Fluorescence*, Plenum Press, New York, N.Y.). The fact that AB forms a dimer in solution simplifies the interpretation of FRET measurements, because there is only one distance between fluorophores in a dimer. If a sufficient number of distance measurements are available, it may be possible to discern the structural organization of the polypeptide within the dimer, albeit at a lower resolution than might be achievable by X-ray crystallography or NMR. Until now, this is the first report in which Aβ amyloid intrinsic fluorescence and FRET between Aβ fluorescent derivatives have been used to study amyloid structure. Different fluorescent Aβ analogs may also be useful for mapping the solvent-accessible surface of the amyloid fibril by quenching studies (Lakowicz, (1983) *Principles of Fluorescence*, Plenum Press, New York, N.Y.).

Moreover, as discussed above, since the aggregation state of Aβ has been shown to be important for in vitro toxicity, molecules that inhibit Aβ aggregation provide candidates for therapeutic strategies based on blocking amyloid deposition. Examples of therapeutic inhibitors are molecules that bind tightly with Aβ monomer and prevent dimerization and molecules that prevent oligomerization of dimers or the extension of fibrils.

Materials

All Aβ peptides analogs were synthesized by fluoren-9-ylmethoxy carbonyl chemistry using a continuous flow semiautomatic instrument as described previously (Burdick et al., (1992) *J. Biol. Chem.* 267:546-554). The peptides were purified by reverse phase high performance liquid chromatography, and the purity and expected structure was verified by electrospray mass spectrometry. Only peptides exhibiting 90% or greater purity with less than 5% of a single contaminant were used. The wild type sequence on which these peptides were based was DAEFRHDSGYEVHHQKLVFFAEDVGSNK-GAIIGLMVGGVV (SEQ ID NO: 1). The sequence of the extended Aβ peptides was DAEFRHDSGYEVHHQKLVFFAEDVGSNK-GAIIGLMVGGVVIA (SEQ ID NO: 2). Cysteine substitution mutants were synthesized simultaneously by the same method, except that, at locations where cysteine was substituted, a portion of the resin was coupled separately with cysteine. $^3$H-Aβ and $^{14}$C-Aβ were synthesized by incorporation of Fmoc-$^3$H-Phe or Fmoc-$^{14}$C-Ala at positions 4 and 2 respectively, yielding specific activities of 200 mCi/mmol for $^3$H-Aβ and 36 mCi/mmol for $^{14}$C-Aβ. 1,5-IAEDANS and FM were obtained from Molecular Probes (Eugene, Oreg.). All other reagents were of the highest analytical grade commercially available. A shorthand notation is used herein to refer to the Aβ analogs that indicates the position of the cysteine substitution with the understanding that all peptides are 40 residues long, and the rest of the sequence is that of wild type Aβ as described in the abbreviations list.

Fluorescence Labeling of Mutant Aβ Peptides with 1,5-IAEDANS and FM

Since Aβ peptides were modified with a single cys at different positions, the sulfydryl-specific reagents FM and 1,5-IAEDANS were used to prepare fluorescent derivatives. The Aβ analog peptides were dissolved in 10 mM MOPS pH 8.5 at a concentration of 25 μM (pH 7.4 in the case of fluorescein labeling). 1,5-IAEDANS or FM was added to this solution from a stock solution of 10 mM at a twenty fold (for 1,5-IAEDANS) or 5-fold (for FM) molar excess over AB. The reaction was allowed to proceed at room temperature in the dark for 6 hours. Free fluorophore was then removed by filtration on a Sephadex G-25 column equilibrated with 10 mM MOPS at pH 7.4. Labeled Aβ was aliquoted, lyophilized, and stored at −20° C. Protein was determined by Coomassie R Protein Assays Reagent (Pierce, Rockford, Ill.). The concentrations of 1,5-IAEDANS or FM were spectrophotometrically determined by using their molar extinction coefficients (5,7 mM$^{-1}$ at 336 nm or 83 mM$^{-1}$ at 490 nm, respectively). The labeling stoichiometry of the final products was 1.0. The stoichiometry was confirmed by laser desorption mass spectrometry that demonstrated that all of the precursor had been converted to a mass appropriate for fluorescent peptide.

Aggregation Measurements

Aggregation was determined using a sedimentation assay as previously described (Burdick et al., (1992) *J. Biol. Chem.* 267:546-554). $^3$H-Aβ (CPM) was mixed with 5 μM fluorescent Aβ and unlabeled A13 at a total concentration of 95 μM and incubated for 48 hours. The amount of sedimentable wild type peptide was determined by scintillation counting, and the amount of sedimentable fluorescent peptide was determined by fluorescence intensity as described herein.

Gel Filtration Chromatography

Gel filtration analysis was performed with a Pharmacia Superdex 75 HR 10/30 column using a Waters 490 multiple wavelength UV absorbance detector and Hewlett Packard 3250 fluorescence detector. Data were collected with a Waters Maxima chromatography data system. The running buffer used was 50 mM Tris, 0.1 M NaCl, pH 7.4 (Buffer A) in the presence of 10% or 2% DMSO. The column was calibrated with the following molecular weight standards: thyroglobulin, bovine serum albumin, ovalbumin, soybean trypsin inhibitor, ubiquitin, aprotinin, and insulin β-chain. The peptides were detected by UV absorbance at 280 nm and by fluorescence at 482 and 520 nm for IAEDANS and FM respectively.

Denaturation of Aβ in DMSO and Refolding

11 μM Aβ or AβC25AEDANS was incubated in increasing concentrations of DMSO, for 1 hour at 24° C. Emission spectra were recorded from 290 to 400 nm upon excitation at 280 nm (or from 340 to 620 nm upon excitation at 336 nm for AβC25AEDANS). Equilibrium was reached after 2 hours of incubation in DMSO. For refolding experiments, samples were incubated in 100% DMSO for 1 hour at room temperature, and refolding was initiated by ten or fifty times dilution of the solvent in Tris buffered solution. The concentration of peptide ranged between 3 and 10 μM.

Absorption and Fluorescence Measurements

Absorption measurements were measured with a Perkin Elmer Lambda 3B UV-Vis spectrophotometer. Fluorescence spectra (excitation band pass 4 nm; emission band pass 8 nm) were measured either on an Aminco SLM 48000 or a SPEX Fluorolog F112A spectrofluorometer. Intrinsic tyrosine fluorescence was measured from 285 to 400 nm upon excitation at 275 nm. For AβC25-AEDANS or in energy transfer experiments excitation was at 330 nm, and the spectra were obtained from 340 to 620 nm. The lifetime measurements for FM were acquired using the 488 nm line of argon ion laser for excitation using a multiharmonic frequency-domain spectrofluorometer (Aminco 48000S).

Fluorescence Resonance Energy Transfer

The efficiency (E) of fluorescence resonance energy transfer (FRET) between probes was determined by measuring the fluorescence intensity of the donor (AβC-AEDANS or Aβ) both in the absence ($F_d$) and presence ($F_{da}$) of the acceptor (AβC-FM or AβY10W), as given by:

$$E = 1 - F_{da}/F_d$$

The efficiency of FRET depends on the inverse sixth power of the distance between donor and acceptor (Lakowicz, (1983) *Principles of Fluorescence*, Plenum Press, New York, N.Y.). This allows FRET measurements to be used with high sensitivity to follow the association of fluorescent-labeled Aβ monomers during refolding of the peptide in aqueous solution. Stock solutions of peptide in DMSO were mixed at an equal molar ratio and diluted 10-fold or 50-fold into 50 mM Tris, pH 7.4, 0.1 M NaCl, and the fluorescence spectra was recorded at various times after dilution. Controls included the donor and acceptor peptides diluted separately and the donor and acceptor mixed with a 10-fold excess of Aβ.

Abbreviations

The following abbreviations are used herein:

1,5-IAEDANS-5-(2-((iodoacetly)amino)ethyl) aminonapthylene-1-sulfonic acid
FM—Fluorescein maleimide
DMSO—Dimethylsulfoxide
AβC25AEDANS—Aβ with cys in position 25 and labeled with 1,5-IAEDANS
AβC7FM—Aβ with cys in position 7 and labeled with FM
AβC34AEDANS—Aβ with cys in position 34 and labeled with 1,5-IAEDANS
AβC4FM—Aβ with cys in position 4 and labeled with FM
AβY10W—Aβ with trp in position 10.

Additional Fluorescent Aβ Peptides

Other fluorescently labeled Aβ peptides possessing the aggregation properties of wild-type Aβ may be synthesized and tested using the techniques described above. In particular, other cysteine-substituted peptides may be made, fluorescently labeled, and tested for aggregation properties (for example, by centrifugation, gel filtration, or FRET analysis). In preferred examples, using the methodologies described herein, Aβ peptides may be cysteine-substituted and fluorescently labeled at any hydrophobic amino acid position. Alternatively, Aβ peptides may be labeled at the free amino group. In addition, Aβ peptides may be produced which have multiple sites labeled, if desired, with different fluorescent tags. Again, aggregation activity is tested, for example, as described herein.

Aβ fragments having cysteine substitutions (for example, those substitutions described above) may also be synthesized, fluorescently labeled, and tested for activity. One preferred Aβ fragment includes amino acids 10-25 of SEQ ID NO: 1.

In addition, any other appropriate fluorescent label may be utilized for peptide synthesis and the methods of the invention. Preferred fluorescent labels include, without limitation, any fluorescent label having a thiol-reactive group. Such fluorescent labels include, for example, thiol-reactive BODIPY, fluorescein, Oregon Green, tetramethylrhodamine, eosin, erythrosin, coumarin, pyridyloxazole, benzoxadiazole, aminonapthalene, pyrene, maleimide, a lanthanide cryptate, a lanthanide chelate, and Texas Red derivatives (commercially available, for example, from Molecular Probes, Eugene, Oreg.).

EXAMPLE 2

Methods of Use for Fluorescently Labeled Amyloid Aβ Peptides

Because the fluorescently labeled peptides described herein possess aggregation properties characteristic of wild type Aβ peptides, they provide useful reagents for detecting or monitoring the formation or existence of amyloid plaques as a means of diagnosing Alzheimer's disease or a predisposition thereto. In one particular example, a test sample of affected tissue (for example, neuronal or vascular tissue) is obtained from a patient. This tissue is then combined with a fluorescent peptide of the invention under conditions that allow Aβ aggregation (for example, those conditions described herein). The sample is washed to remove unbound peptide, and detection of the fluorescent label in association with the tissue sample is taken as an indication that Aβ deposits are present in the patient sample. In these assays, a negative control sample that is free of amyloid plaques (for example, from an unaffected individual) and one or more positive control samples containing known quantities of amyloid plaques are preferably assayed in parallel, and the results from the patient sample compared to those controls. If desired, in these assays, the degree of fluorescent output may be quantitated by standard techniques as an indication of the extent of amyloid plaque formation. This technique is particularly useful for monitoring the progression of disease in an Alzheimer's patient, or the amelioration of disease in response to therapeutic treatment.

For this assay, patient tissue samples may be obtained from any site at which amyloid plaques have been shown to occur including, without limitation, any brain tissue (for example, cerebral cortex, amygdala, and hippocampal tissue), vascular tissue, or neuronal tissue (for example, nasal epithelium). Tissue samples may be tested as thin sections or tissue homogenates. Fluorescent peptide may be added at any appropriate concentration, preferably between 0.1 μM and 25 μM, and more preferably between 0.1 μM and 3 μM. Measurement of fluorescent output is accomplished by any standard technique, for example, fluorescence microscopy or flow cytometry. Preferred fluorescent labels for diagnostic use include, without limitation, any thiol-reactive probe, for example, any BODIPY, fluorescein, Oregon Green, tetramethylrhodamine, eosin, erythrosin, coumarin, pyridyloxazole, benzoxadiazole, aminonapthalene, pyrene, maleimide, a lanthanide cryptate, a lanthanide chelate, or Texas Red derivative (commercially available, for example, from Molecular Probes, Eugene, Oreg.).

In addition to diagnostic utilities, the fluorescent peptides described herein are also useful as reagents for screening assays for the identification of compounds that modulate Aβ aggregation. Typically, such screening assays are carried out for the purpose of isolating or identifying compounds that inhibit Aβ aggregation, but may also be used to identify compounds that enhance aggregation.

In one approach, a fluorescent peptide of the invention is placed in contact with an amyloid plaque (for example, from a patient sample) under conditions that allow aggregation. The complex is then treated with candidate modulatory compounds (preferably, inhibitory compounds), and those compounds which affect the ability of the fluorescent peptide to aggregate with the amyloid plaque are selected. With respect to inhibitory compounds, candidate compounds may be added following aggregation of the fluorescent peptide with the amyloid plaque to identify those compounds capable of disrupting or disaggregating existing plaques. Alternatively, the candidate compound may be added to a plaque sample at the same time as the fluorescent peptide to identify compounds capable of interfering with further plaque formation. In these assays, aggregation is measured by association of fluorescent label with the tissue sample. As discussed above, the amyloid plaque used in this assay may be presented as a tissue sample (for example, a thin section), or a tissue homogenate may be used. Also, as discussed above, an untreated sample may be used for comparison purposes in these assays.

In an alternative approach to the identification of modulatory compounds, aggregation of the fluorescent peptides of the invention may be assayed directly, with changes in aggregation pattern, conditions, or reaction times used to identify modulatory compounds. As described herein, the fluorescent Aβ peptides of the invention exhibit aggregation properties characteristic of wild type Aβ. Accordingly, candidate compounds may be added to a solution of fluorescent Aβ, either before or after initiation of peptide aggregation, and compounds identified that modulate the ability of these peptides to aggregate. Fluorescent Aβ aggregation is measured by any appropriate means, for example, any of the methods described herein including, without limitation, fluorescence resonance energy transfer, centrifugation, or gel filtration. Alternatively, unlabeled Aβ may be attached to a solid support (for example, a test tube, bead, column, or microtiter dish), and fluorescent Aβ added, either before or in conjunction with a test modulatory compound. Aggregation is then monitored in response to the compound. In this assay, the extent of aggregation is indicated by the amount of fluorescent label associated with the solid support following appropriate washing. In both of these exemplary approaches, a negative control is preferably included for comparison purposes, in which no candidate compound is added.

In general, candidate modulatory compounds may be identified from large libraries of natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

Compounds identified as being capable of inhibiting Aβ aggregation are useful as therapeutics, or for the design of therapeutics, for Alzheimer's disease. If desired, such compounds may be further tested for efficacy in Alzheimer's animal models.

What is claimed is:

1. A method for detecting or monitoring an amyloid aggregate in a sample, said method comprising
   (a) contacting said sample with an aggregating amyloid Aβ peptide wherein a cysteine amino acid replaces an amino acid of a wild-type Aβ peptide and further wherein said cysteine amino acid is covalently bonded to a fluorescent label; and
   (b) detecting said fluorescent label in association with said sample as an indication of an amyloid aggregate.

2. The method of claim 1, wherein said method is carried out to diagnose Alzheimer's disease or a predisposition thereto.

3. The method of claim 1, wherein said cysteine amino acid replaces a hydrophobic amino acid.

4. The method of claim 1, wherein said cysteine amino acid replaces an internal amino acid.

5. The method of claim 1, wherein said fluorescent label is a thiol-reactive fluorescent dye.

6. The method of claim 1, wherein said fluorescent label is chosen from 5-(2-((iodoacetyl)amino)ethyl) aminonapthylene-1-sulfonic acid (1,5-IEDANSI or fluorescein.

7. The method of claim 1, wherein said fluorescent label is selected from the group consisting of dipyrromethene boron fluoride (Bodipy), fluorescein thiosemicarbazide (FTC)., sulforhodamine 101 acid chloride (Texas Red)., phycoerythrin, rhodamine, carboxytetramethylrhodamine 46-diamino-2-phenylindole (DAPI), an indopyras dye, pyrenvioxytrisulfonic acid (Cascade Blue)., 514 carboxylic acid (Oregon Green)., eosin, erythrosin, pyridyloxazole, benzoxadiazole, aminonapthalene, pyrene, maleimide, a coumarin, 4-fiuoro-7-rtitrobenzofurazan (N B D)., 4-amino-N-[3-(vinylsulfonyl)-phenyl]naothalimide-3,6-disulfonate) (Lucifer Yellow), propidium iodide, a porphyrin, a cyanine dye ($CY^3$, $CY^5$, $CY^9$) a lanthanide cryptate, a lanthanide chelate, a derivative thereof, and an analog thereof.

8. The method of claim 1, wherein said wild type Aβ peptide is a human wild type Aβ peptide.

9. The method of claim 8, wherein said wild type Aβ peptide has an amino acid sequence of SEQ ID NO: 1.

10. The method of claim 8, wherein said wild type Aβ peptide has an amino acid sequence of SEQ ID NO: 2.

11. The method of claim 1, wherein said cysteine amino acid replaces a phenylalanine amino acid at position 4 of SEQ ID NO: 1 or SEQ ID NO. 2.

12. The method of claim 1, wherein said cysteine amino acid replaces an aspartic acid amino acid at position 7 of SEQ ID NO: 1 or SEQ ID NO: 2.

13. The method of claim 1, wherein said cysteine amino acid replaces a glycine amino acid at position 25 of SEQ ID NO: 1 or SEQ ID NO:2.

14. The method of claim 1, wherein said cysteine amino acid replaces a leucine amino acid at position 34 of SEQ ID NO: 1 or SEQ ID NO: 2.

* * * * *

UNITED STATES PATENT AND TRADEMARK OFFICE
CERTIFICATE OF CORRECTION

PATENT NO. : 6,770,448 B2
DATED : August 3, 2004
INVENTOR(S) : Charles Glabe and William Garzon Rodriguez It is certified that error appears in the above-identified patent and that said Letters Patent is hereby corrected as shown below:

Title page,
Item [56], References Cited, OTHER PUBLICATIONS, "Burdick et al." reference, replace "Amyloid Analogs" with -- Amyloid Peptide Analogs --; and "Wisniewski and Franglone" reference, replace "Amyloid"*Neurosci.*" with -- Amyloid" *Neurosci.* --.

Column 1,
Lines 43-44, replace "*Biophisical*" with -- *Biophysical* --.

Column 2,
Line 34, replace "fluorescent" with -- fluorescein --;
Line 37, replace "pvrenyloxytrisulfonic" with -- pyrenyloxytrisulfonic --; and
Line 43, after "$CY^9$)," insert -- a lanthanide cryptate --.

Column 3,
Line 1, replace "aminonapthviene-1 -sulfonic" with
-- aminonapthylene-1-sulfonic --;
Line 6, replace "4, 6diamino-2-phenylifldole" with
-- 4, 6-diamino-2-phenylindole --;
Line 8, replace "(Cascade Blue, 514 carboxylic" with -- (Cascade Blue), 514 caboxylic acid --;
Line 11, replace "7-nitrobenfurazan (NBD), 4-amino-N[3- (vinylsulfonyl)"
with -- 7-nitrobenzofurazan (NBD), 4-amino-N-[3-(vinylsulfonyl) --;
Line 12, replace "(phenyl]" with -- phenyl] --;
Line 12, replace "(Lucifer Yellow," with -- (Lucifer Yellow), --;
Line 13, replace "$CY^9$ ," with -- $CY^9$), --;
Line 46, replace "Aγ" with -- Aβ --;
Line 54, replace "iodoacetvI" with -- iodoacetyl --;
Line 55, replace "aminonaothylene" with -- aminonapthylene --;
Line 55, replace "IEDANSI" with -- IEDANS) --;
Line 56, replace "Light" with -- light --;
Line 58, replace "Bodipyl" with -- Bodipy) --;
Line 60, replace "carboxytetramethylrodamine" with
-- carboxytetramethylrhodamine --;
Line 63, replace "Greeni" with -- Green) --;
Line 67, after "Porphyrin" insert -- , --; and
Line 67, replace "($CY^3$, $CY_5$, $CY^9$," with -- ($CY^3$, $CY^5$, $CY^9$), --.

UNITED STATES PATENT AND TRADEMARK OFFICE
CERTIFICATE OF CORRECTION

PATENT NO. : 6,770,448 B2
DATED : August 3, 2004
INVENTOR(S) : Charles Glabe and William Garzon Rodriguez It is certified that error appears in the above-identified patent and that said Letters Patent is hereby corrected as shown below:

Column 7,
Line 6, replace "*Biophisical*" with -- *Biophysical* --;
Lines 11 and 19, replace "74222" with -- 7422 --; and
Line 52, replace "AB" with -- Aβ --.

Column 10,
Lines 2 and 24, replace "*Biophisical*" with -- *Biophysical* --; and
Line 41, replace "seem" with -- seems --.

Column 11,
Line 18, replace "A13" with -- Aβ --; and
Line 23, replace "AB" with -- Aβ --.

Column 12,
Line 19, replace "AB" with -- Aβ --; and
Line 37, replace "A13" with -- Aβ --.

Column 17,
Line 21, after "peptide" insert -- , --;
Line 38, replace "IEDANSI" with -- IEDANS) --;
Line 43, replace "(FTC).," with -- (FTC), --; and
Line 43, replace "(Texas Red).," with -- (Texas Red), --.

UNITED STATES PATENT AND TRADEMARK OFFICE
CERTIFICATE OF CORRECTION

PATENT NO.   : 6,770,448 B2
DATED        : August 3, 2004
INVENTOR(S)  : Charles Glabe and William Garzon Rodriguez It is certified that error appears in the above-identified patent and that said Letters Patent is hereby corrected as shown below:

Column 18,
Line 17, replace "46" with -- 4,6 --;
Line 18, replace "pyrenvioxyltrisulfonic" with -- pyrenyloxytrisulfonic --;
Line 18, replace "(Cascade Blue).," with -- (Cascade Blue), --;
Line 19, replace "(Oregon Green).," with -- (Oregon Green), --;
Line 21, replace "fiuoro-7-rtitrobenzofurazan (N B D).," with
-- fluoro-7-nitrobenzofurazan (NBD), --; and
Line 22, replace "CY$^9$)" with -- CY$^9$), --.

Signed and Sealed this

Seventeenth Day of May, 2005

JON W. DUDAS
*Director of the United States Patent and Trademark Office*